United States Patent
Zanghi et al.

(10) Patent No.: US 10,624,937 B2
(45) Date of Patent: Apr. 21, 2020

(54) COMPOSITIONS AND METHODS FOR INFLUENCING RECOVERY FROM STRENUOUS PHYSICAL ACTIVITY

(71) Applicant: NESTEC SA, Vevey (CH)

(72) Inventors: Brian Michael Zanghi, Ballwin, MO (US); Arleigh James Reynolds, Salcha, AK (US); Rondo Paul Middleton, Creve Coeur, MO (US)

(73) Assignee: Societe des Produits Nestle SA, Vevey (CH)

( * ) Notice: Subject to any disclaimer, the term of this patent is extended or adjusted under 35 U.S.C. 154(b) by 680 days.

(21) Appl. No.: 14/797,766

(22) Filed: Jul. 13, 2015

(65) Prior Publication Data

US 2015/0313262 A1    Nov. 5, 2015

Related U.S. Application Data

(63) Continuation of application No. 12/735,651, filed as application No. PCT/US2009/000741 on Feb. 5, 2009, now Pat. No. 9,107,867.

(60) Provisional application No. 61/063,918, filed on Feb. 7, 2008.

(51) Int. Cl.
| | |
|---|---|
| A23K 50/00 | (2016.01) |
| A23K 20/163 | (2016.01) |
| A61K 36/06 | (2006.01) |
| A23K 50/40 | (2016.01) |
| A23K 10/18 | (2016.01) |
| A23K 20/147 | (2016.01) |
| A23K 20/142 | (2016.01) |
| A23L 33/19 | (2016.01) |
| A23L 33/10 | (2016.01) |
| A23L 33/185 | (2016.01) |
| A23L 33/105 | (2016.01) |
| A23L 33/175 | (2016.01) |

(52) U.S. Cl.
CPC ............ *A61K 36/06* (2013.01); *A23K 10/18* (2016.05); *A23K 20/142* (2016.05); *A23K 20/147* (2016.05); *A23K 20/163* (2016.05); *A23K 50/40* (2016.05); *A23L 33/10* (2016.08); *A23L 33/105* (2016.08); *A23L 33/175* (2016.08); *A23L 33/185* (2016.08); *A23L 33/19* (2016.08)

(58) Field of Classification Search
CPC ........ A23L 1/0522; A23L 1/097; A23L 1/305; A23L 1/00; A23L 1/0017; A23L 1/0026; A23L 33/10; A23L 33/19; A23L 33/175; A23L 33/105; A23L 33/185; A23K 1/1846; A23K 1/1643; A23K 1/1631; A23K 1/1634; A23K 1/009; A23K 20/142; A23K 20/147; A23K 20/163; A23K 50/40; A23K 10/18; A61K 36/06
See application file for complete search history.

(56) References Cited

U.S. PATENT DOCUMENTS

| | | | | |
|---|---|---|---|---|
| 2,991,181 | A | * | 7/1961 | Benjamin ............... A23L 7/135 426/560 |
| 5,194,284 | A | * | 3/1993 | Chiu ...................... A21D 2/186 426/589 |
| 5,795,602 | A | | 8/1998 | Craig et al. |
| 8,034,372 | B2 | * | 10/2011 | Sidebottom .......... A23K 1/1603 424/442 |
| 2004/0047896 | A1 | * | 3/2004 | Malnoe ................. A23K 1/1846 424/439 |
| 2004/0219188 | A1 | | 4/2004 | Comer et al. |
| 2004/0096547 | A1 | | 5/2004 | Ferruzzi |
| 2004/0175413 | A1 | | 9/2004 | Sidebottom et al. |
| 2005/0226960 | A1 | * | 10/2005 | Boice ...................... A23L 33/26 426/72 |
| 2006/0005285 | A1 | | 1/2006 | Strissel et al. |
| 2008/0008801 | A1 | | 1/2008 | Barnekow et al. |
| 2008/0317886 | A1 | * | 12/2008 | Sparkman ............. A23L 1/3002 514/1.1 |

FOREIGN PATENT DOCUMENTS

| | | |
|---|---|---|
| CN | 1756488 A | 5/2006 |
| JP | 2006519617 T | 8/2006 |
| JP | 2007508343 T | 4/2007 |
| WO | 0048475 A1 | 8/2000 |
| WO | 200101789 A1 | 1/2001 |
| WO | 2005039318 A1 | 5/2005 |
| WO | 2007064618 A1 | 6/2007 |
| WO | 2007126990 A2 | 11/2007 |

OTHER PUBLICATIONS

International Search Report and Written Opinion, PCT/US09/00741 dated Apr. 22, 2009.
Extended European Search Report 09708017.0, dated Dec. 22, 2011.

* cited by examiner

*Primary Examiner* — Lakshmi S Channavajjala
(74) *Attorney, Agent, or Firm* — Ronald A. Burchett; Julie M. Lappin

(57) ABSTRACT

Compositions and methods for influencing the recovery of an animal from the effects of strenuous physical activity. The compositions generally comprise about 4% to 6% readily absorbable carbohydrate; about 10% to 30% maltodextrins; about 20% to 50% starch, for a total of about 40% to 80% carbohydrate; about 20% to about 40% protein; and optionally one or more antioxidants. The methods generally comprise administering the composition to an animal within the period from about 120 minutes before initiation of or 120 minutes after completion of the physical activity.

6 Claims, No Drawings

COMPOSITIONS AND METHODS FOR INFLUENCING RECOVERY FROM STRENUOUS PHYSICAL ACTIVITY

CROSS REFERENCE TO RELATED APPLICATIONS

This application is a Continuation of U.S. patent application Ser. No. 12/735,651 flied on Oct. 27, 2010, which is a national stage application under 35 USC § 371 of PCT/US09/00741 filed on Feb. 5, 2009 and claims priority to U.S. Provisional Application No. 61/063,918 filed Feb. 7, 2008, the disclosures of which are incorporated herein by this reference.

BACKGROUND OF THE INVENTION

Field of the Invention

The invention relates generally to compositions and methods for influencing recovery from strenuous physical activity and particularly to compositions comprising carbohydrates, amino acids, or antioxidants and the use of such compositions to influence recovery from strenuous physical activity in animals.

Description of Related Art

Physical exhaustion in animals results from physical activity depending on intensity and/or duration. Strenuous activities, including work, sports, exercise, and the like have the potential to produce the physical or biochemical changes associated with physical exhaustion. For some animals, activities like hunting, hacking, sled racing, agility trials, and play activities can lead to physical exhaustion. Other activities, such as parturition in pregnant animals, and excessive non-specific activities like temporary placement in a kennel facility can also result in physical exhaustion. Physical exhaustion is associated with a variety of physical, cellular and biochemical changes, beginning with depletion of muscle and liver glycogen stores. Liver glycogen is a source of glucose for cellular function in the muscle, brain, and other tissues required to support bouts of exercise or physical activity.

Such physical activity and depletion of glycogen are also associated with muscle-fiber damage, muscle soreness, muscle inflammation, and/or fatigue. This damage results, at least in part, from the disruption of cell membrane integrity and subsequent cell content leakage, along with damage from oxidative stress. Elevated levels of creatine kinase (CK, also known as creatine phosphokinase or CPK)) and lactate dehydrogenase (LDH) following exercise are hallmark indicators of activity-induced muscle-fiber damage and disruption of muscle membrane integrity. Strenuous or excessive physical activity is also associated with an elevation of lactic acid that additionally contributes to muscle soreness (for example, delayed-onset muscle soreness) and fatigue.

Products are available that address the problem of replenishing exercise-depleted glycogen stores with carbohydrates to improve exercise recovery, see WO 2004/077961. However, studies in humans have demonstrated that dietary supplementation of carbohydrates alone after exercise cannot improve recovery from muscle damage.

Strenuous physical activity such as exercise also results in a significant amount of oxidative stress. It is known that inflammation and oxidative stress are linked via muscle metabolism and muscle damage, particularly during exercise. Because oxidative stress and inflammation have traditionally been associated with fatigue and impaired recovery from exercise, research has focused on nutritional strategies aimed at reducing these effects. Currently, antioxidants such as vitamins E and C are widely recommended to attenuate the effects of exercise-induced oxidative stress. However, alternative antioxidants are needed because both vitamins C and E can act as pro-oxidants under certain conditions. Pro-oxidants enhance rather than reduce the formation of reactive oxygen and nitrogen species.

Studies in greyhounds have demonstrated a decrease in performance with vitamin E dietary supplementation. Other studies have shown that sled dogs administered diets supplemented with vitamin E and vitamin C showed no improvement in post-exercise indices of oxidative stress when compared to sled dogs given no antioxidant supplements. WO2004077961 discloses methods and composition for helping animals recover from the results of strenuous activity. The methods entail administering a composition comprising a mixture of carbohydrates to provide readily assimilated or available energy, such as glucose, a source of vitamins, minerals, and antioxidants that are expended more quickly during the strenuous activity than at other times, or required in response to the demands of the activity.

There is, however, a need for new compositions and methods that influence recovery from strenuous physical activity in animals, e.g., exercise recovery.

SUMMARY OF THE INVENTION

It is, therefore, an object of the present invention to provide compositions and methods useful for influencing recovery from strenuous physical activity in animals.

It is another object of the present invention to provide compositions and methods useful for (a) minimizing the rate or extent of one or more deleterious physical, cellular, or biochemical changes that result from strenuous physical activity or (b) promoting recovery from such changes.

It is a further object to provide compositions and methods to measurably reduce or minimize one or more aspects of damage or results from strenuous physical activity in animals, including muscle fiber damage, decrease or loss of membrane integrity in muscle or other tissue, muscle soreness, stress hormone production, inflammation, or fatigue, or to promote recovery from such damage or results.

It is a further object of the invention to provide kits for influencing recovery from strenuous activity in an animal, as well as kits for preparing compositions for influencing recovery and for use in the methods described herein.

It is another object of the invention to provide a package comprising a composition provided herein and a label, logo, graphic or the like affixed to the package indicating the contents of the package and/or the benefits of administering the composition to an animal for the purposes of influencing recovery from strenuous physical activity.

One or more of these and other objects are achieved using novel compositions and methods for influencing recovery from strenuous physical activity in animals. Generally, the compositions comprise about 4% to 6% readily absorbable carbohydrate; about 10% to 30% maltodextrins; and about 20% to 50% starch, for a total of about 40% to 80% carbohydrate; about 20% to about 40% protein; and optionally one or more antioxidants.

These and other and further objects, features, and advantages of the present invention will be readily apparent to those skilled in the art.

DETAILED DESCRIPTION OF THE INVENTION

Definitions

The following abbreviations may be used herein: AAS, Amino Acid Score; ALT, alanine transaminase; BCAA branched-chain amino acids; BUN, blood urea nitrogen; BV, Biological Value; CK, creatine kinase; Ca, calcium; DE, dextrose equivalent; GRAS, generally recognized as safe; K, potassium; LDH, lactate dehydrogenase; MCTs, medium chain triglycerides; NSAIDs, non-steroidal anti-inflammatory drugs; PD, Protein Digestibility %; PDCAAS, Protein Digestibility Corrected Amino Acid Score; PER, Protein Efficiency Ratio; and TCA, tricarboxylic acid cycle.

The term "individual" when referring to an animal means an individual animal of any species or kind.

The term "animal" means any animal that could benefit from one or more of the compositions and methods of the provided herein, particularly an animal that could benefit from methods and compositions that are useful for the recovery from strenuous physical activity, e.g., exercise recovery. Thus, the instant disclosure relates to any animal, preferably a mammal. Unless otherwise specified, or clear from the context, the term "mammal" herein includes human. The term "animal" is used in a general sense and means a human or other animal, including avian, bovine, canine, equine; feline, hicrine, lupine, murine, ovine, and porcine animals. The term "companion animal" means any domesticated animal, and includes, without limitation, cats, dogs, rabbits, guinea pigs, ferrets, hamsters, mice, gerbils, horses, cows, goats, sheep, donkeys, pigs, and the like. Certain embodiments in which human animals are expressly excluded, or clearly excluded by the context, may be preferred herein. In certain embodiments, companion animals are preferred, for example, dogs and cats. For example, certain canine companions are subjected to physical activity that can be strenuous, particularly canines that are used for work, such as sledding or carting dogs, police work, rescue, tracking, sport, agility, and exercise.

The term "physical activity" includes any activity that, when engaged in by an animal, tends to reduce or draw down liver and/or muscle glycogen. "Strenuous physical activity" is physical activity that, when engaged in for a period or with sufficient frequency, or without sufficient rest, tends to substantially or completely deplete liver and/or muscle glycogen. The skilled artisan will appreciate that the tendency of any activity to partially, substantially or completely deplete glycogen is a function of both the duration and the intensity of the activity. The amount of time (duration) required varies depending on intensity which can be a function of the type of physical activity, the amount of resistance or the amount of muscle work required, whether the activity requires the use of large or small muscle groups or the whole body, the rate at which the activity is performed, and the like. It is evident that most physical activities can become strenuous when engaged in for sufficient time, or with sufficient intensity. Examples of physical activity include various types of work, play, exercise, conditioning, physical skill development or improvement, rehabilitation, walking, running (or other means or speeds of self-transportation), competitive or non-competitive sports, and related activities. Many biological functions or processes can also be physically demanding and, thus, constitute physical activity as used herein including giving birth, and "fight or flight" response (i.e., stress response) to physical or psychological stressors, injury and/or healing from trauma, infection, and the like, and many other biological activities. The skilled artisan will appreciate that because of factors such as genetic differences, adaptation, conditioning response, and the like, a physical activity may not be equally strenuous for any two animals, and thus, controlled studies and objective measurements are generally preferable (where suited) to anecdotal evidence or perceived exertion as measures of whether or not a particular activity is strenuous, or whether recovery has been influenced by a particular composition or method.

The term "exercise" means a type of physical activity undertaken by an animal or caused to be undertaken by an animal for a particular purpose such as general health, fitness, weight management, improving a particular aspect of health or fitness, strengthening, improving a physical skill or set of skills, improving a function, rehabilitating an injury, and the like. Exercise can be performed on a regular basis, for example daily, thrice per week, or once per week. Frequencies of exercise less than once per week are considered "occasional" exercise. Other patterns of exercise are also recognized and contemplated for use herein. The compositions and methods are useful with exercise, whether regular or occasional. The methods and compositions described herein are particularly useful where the animal is not yet completely conditioned to the exercise or activity, and thus is more likely to be subject to one or more deleterious or undesired physical, cellular, or biochemical changes resulting from such exercise or activity. They are also useful for improving performance even in conditioned animals because preferably they influence faster or more complete recovery in preparation for the next strenuous activity. Also they preferably allow improved performance during the activity because of reduced damage from preceding exercise or activity session.

The term "recovery" means recovery from any strenuous physical activity, including exercise. Recovery is a process of returning to a normal or a pre-activity state following physical activity, especially strenuous physical activity. Recovery encompasses many aspects of the physical, cellular, and biochemical effects of strenuous physical activity. Various indicators may be used to establish that a particular animal has recovered, or is recovering from strenuous physical activity. To assess recovery, baseline, normal, or pre-activity (or pre-exercise) states can be compared with a post-exercise state within an individual animal, or group of animals. Among animals subjected to a particular activity, work, exercise, regimen, or the like, comparisons may be made among individuals or treatment groups. Useful comparisons may at times he made between animals subjected to exercise, and those who have not, where all animals receive a particular treatment. For example, depending on the time point observed, in recovered or recovering animals, frequently blood glucose levels have been returned to normal or pre-activity levels, or are returning to normal or pre-exercise levels in the animal during recovery. As discussed above, recovery can be assessed relative to a control animal or group of animals. In some cases, liver and/or muscle glycogen supplies in a recovered or recovering animal are at least partially replenished, or are being replenished during recovery. Measures of activity-induced or exercise-induced cellular leakage, membrane damage, disruption of membrane integrity, muscle fiber damage, oxidative stress or damage, inflammation, and fatigue can return to normal or pre-exercise levels, or be improved or improving, for example, relative to a control animal that is comparably exercised but did not receive a treatment of interest. Measurements of biomarkers of damage or stress from physical activity, such as the blood levels of certain chemicals (e.g., lactic acid), ions (e.g., calcium or potassium), enzymes (e.g., creatine kinase (CK) or lactate dehydrogenase (LDH)) may be used to assess aspects of recovery in animals or groups of animals. In certain embodiments herein, "recovery" is improved in treated animals, i.e. animals receiving a composition for influencing recovery, wherein the animals receive at least some portion of the composition prior to the start of the activity or exercise, e.g., within a window of about 30, 60, 90, or even 120 minutes before the start of the activity, or during the activity prior to the completion thereof. In such embodiments, recovery may in part be improved by the prevention, minimization, or reduction of the rate of, a physical, cellular, or biochemical change in the animal during or after the activity. For example, pre-activity consumption may help maintain blood glucose levels longer, or decrease the rate or extent of the activity-induced blood glucose drop. The animal's recovery may thus be enhanced relative to an animal not receiving the composition, or only receiving the composition after the completion of the activity or exercise.

The terms "influence" "influences" and "influencing" used herein with respect to recovery from physical activity, indicates that a particular composition or method has some measurable effect on such recovery, for example, the time course, rate, extent, or the like, of recovery from physical activity. A compound or method can also "influence recovery" by decreasing the rate, amount, extent, or the like of damage caused by strenuous physical activity. Any measurable decrease in damage, whether director indirect, as a result attributable to the use of a composition or method, "influences" the recovery from the physical activity that caused the damage. A compound or treatment "influences" recovery from physical activity when there is measurable alleviation of at least one indicia of the effects of or damage resulting from physical activity, or measurable improvement in at least one indicia of recovery. For example, improvement in the rate or extent of return of blood glucose levels to normal or pre-activity levels, reduction of lactate levels, or the increase in lactate clearance, and the like are each sufficient indicators of a positive influence of a composition or treatment tan recovery.

The term "effective amount" means an amount of a compound, material, composition, medicament, or other material that is effective to achieve a particular biological result. Such results include, but are not limited to, one or more of the following: influencing recovery from strenuous physical activity, reducing or minimizing the damage caused directly or indirectly by physical activity, particularly strenuous physical activity, or preventing, reducing, or minimizing at least one physical, cellular, or biochemical consequence, symptom, affect, indicia, or the like of strenuous physical activity. in certain embodiments, an effective amount of a composition decreases protein catabolism, or art-recognized consequence, symptom, affect, or indicia thereof, or it may stimulate protein anabolism, or art-recognized consequence, symptom, affect, or indicia thereof. In some embodiments, an amount can be effective when administered or consumed prior to participation in physical activity. In other embodiments, an effective amount can be administered or consumed during participation in the physical activity, or for example during a brief break or rest period. In still other embodiments, an effective amount can be administered or consumed within a specified window of time after the completion of most or all of the physical activity. Combinations of the foregoing are possible such that an effective amount can be administered or consumed before, during, or after the physical activity, or the total effective amount can be administered or consumed in more than one portion administered or consumed at more than one time before, during, or after the completion of the physical activity. For various reasons, preferably the effective amount is administered or consumed not later than about 60 to 120 minutes after the completion of the physical activity. Preferably, the composition is consumed immediately at the conclusion of the physical activity, or within a period of 1, 5, 10, 15, 20, 30, 40, 45, 50, or 55 minutes, or any intermediate values at less than about 1 hour. In other embodiments it is consumed in 60, 70, 80, 90 or less minutes after completion, while in still others it may be consumed within 100, 110, or 120 minutes of the completion. Some influence may accrue by consumption outside of this window of time, however, the skilled artisan will appreciate that the potential benefits decrease and the risk of delayed recovery increase as the time extends well beyond the completion of the strenuous activity.

The term "food" or "food product" or "food composition" means a product or composition that is intended for ingestion by an animal, including a human, and provides nutrition to the animal. The term "food" includes any food, feed, snack, food supplement, treat, meal substitute, or meal replacement, whether intended for a human or another animal. "Food" encompasses such products in any form, solids, powders, liquids, gels, or mixtures or combinations thereof. "Animal food" includes food or feed intended for any domesticated or wild species. In preferred embodiments, a food for an animal represents a nutritionally complete food composition, e.g., a pelleted, extruded, or dry food. Examples of such animal foods include extruded pet foods, such as foods for dogs or cats. Other examples are a mixture of two or more of the dry ingredients, or an uncooked dough that includes some or all of the ingredients, The term "maltodextrin" is a term of art that refers to a group of distinct carbohydrates, for example starch degradation products of varying length/complexity, and not a specific compound with a single chemical structure. The U.S. Food and Drug Administration gives maltodextrin GRAS status and defines maltodextrin as "a nonsweet nutritive saccharide polymer that consists of D-glucose units linked primarily by [alpha]-1-4 bonds and that has a dextrose equivalent (D.E.) of less than 20." Maltodextrins can be prepared in a variety of ways from a variety of starting materials. Preferred for use herein are maltodextrins having about DE of about 5 to 20, derived from starch such as corn starch, potato starch, rice starch, and the like. Mixtures of more than one maltodextrin are useful herein, thus sometimes the singular form "maltodextrin" refers to one or more different maltodextrins.

The term "food product formulated for human consumption" means any composition specifically intended for ingestion by a human being. The term "pet food" or "pet food composition" means a composition intended for consumption by animals, preferably by companion animals. A "complete and nutritionally balanced pet food" is one that contains all, known required nutrients for the intended recipient or consumer of the food, in appropriate amounts and proportions, based for example on recommendations of recognized authorities in the field of companion animal nutrition. Such foods are therefore capable of serving as a sole source of dietary intake to maintain life or promote production, without the addition of supplemental nutritional sources. Nutritionally balanced pet food compositions are widely known and used in the art.

The term "dietary supplement" means a product that is intended to be ingested in addition to the normal animal diet. Dietary supplements may be in any form, e.g., solid, liquid, gel, tablets, capsules, powder, and the like. Preferably they are provided in convenient: dosage forms. In some embodiments they are provided in bulk consumer packages such as hulk powders, liquids, gels, or oils. In other embodiments, supplements are provided in hulk quantities to be included in other food items such as snacks, treats, supplement bars, beverages and the like.

The terms "administering" or "administration" include self-administration in addition to administration to another animal, for example, a caretaker may administer a food product, composition, medicament, or the like to a companion animal. A caretaker may also ingest or consume a food product, composition, medicament or the like, thereby administering that product, composition, or medicament to himself or herself.

The term "regular basis" with respect to the administration of the compositions described herein means the compositions are administered before, during, or after periods of physical activity, particularly strenuous activity. Thus, if an animal undergoes strenuous physical activity daily, then the composition is preferably consumed at least once daily. If the animal undergoes strenuous physical activity for example, 2 or 3 times per week, then the consumption or administration of the composition would be at least that frequent. More frequent dosing or consumption, such as twice or three times weekly, is preferred in certain embodiments. Also preferred are regimens that comprise at least once daily consumption, even where strenuous physical activity is less frequent than once daily, or even only occasional, as defined herein. The skilled artisan will note the caloric content of the composition should be taken into consideration when determining an animal's overall caloric and nutritional requirements. The skilled artisan will appreciate that the blood level of a compound or certain metabolites of that compound or which result after the consumption of that compound, may be a useful tool for assessing or determining dosing frequency. For example, for determining dosage or dosage frequency, determinations of evidence of muscle damage, or blood glucose measurements or lactate levels may provide useful information. A frequency that allows maintenance of a desired blood level of the measured compound within acceptable ranges is useful herein. To minimize damage and influence recovery, the composition should be used at least with the same frequency as strenuous physical activity is undertaken.

The term "long-term administration" means periods of repeated administration or consumption in excess of one month with each occurrence of strenuous or prolonged physical activity. Periods of longer than two, three, or four months are preferred for certain embodiments, for example with certain companion animals, such as working dogs, hunting dogs, and sled dogs. Also preferred are more extended periods that include longer than 5, 6, 7, 8, 9, or 10 months, especially during periods of intense training. Periods in excess of 11 months or 1 year are also suitable, as are longer term use extending over 1, 2, 3, or more years.

The term "oral administration" or "orally administering" means that the animal ingests, or a human is directed to feed, or does feed, the animal one or more of the compositions described herein. Wherein a human is directed to feed the composition, such direction may be that which instructs and/or informs the human that use of the composition may and/or will provide the referenced benefit, for example, enhancing recovery, minimizing damage from strenuous physical activity cognitive function, improving liver function, increasing daytime activity, improving learning, improving attention, improving social behavior, improving motor performance, and/or improving cerebrovascular function, or preventing, reducing, or delaying a decline in such foregoing functions or qualities. Such direction may be oral direction (e.g., through oral instruction from, for example, a physician, veterinarian, or other health professional, or radio or television media (i.e., advertisement), or written direction (e.g., through written direction from, for example, a physician, veterinarian, or other health professional (e.g., prescriptions), sales professional or organization (e.g., through, for example, marketing brochures, pamphlets, or other instructive paraphernalia), written media (e.g., internet, electronic mail, website, or other computer-related media), and/or packaging associated with the composition (e.g., a label present on a container holding the composition), or combination thereof (e.g., label or package insert with directions to access a website for more information).

The term "recovery agents" means any compound, composition, drug, nutritional or dietary supplement, or other material useful for influencing recovery from strenuous physical activity in animals, e.g., influencing exercise recovery.

The term "in conjunction" means that a composition for influencing recovery from strenuous activity, a food composition, medicament, drug, recovery agent, or other compound or composition described herein are administered to an animal (1) together in a food composition or (2) separately at the same or different frequency using the same or different administration routes at about the same time or periodically. "Periodically" means that the agent is administered on a dosage schedule acceptable for a specific agent and that the food is fed to an animal routinely as appropriate for the particular animal. "About the same time" generally means that the food and agent are administered at the same time or within about 72, 48, 24, 12, 6, 4, or 2 hours of each other. "In conjunction" specifically includes administration schemes wherein a recovery agent is administered for a predetermined, prescribed, or desired period, and the compositions disclosed herein are administered within a defined window of time before, during, or after strenuous physical activity, the window being between about 60 to 120 minutes before the start of and after the completion of the strenuous activity.

The term "single package" means that the components of a kit are physically associated, in or with one or more containers, and considered a unit for manufacture, distribution, sale, or use. Containers include, but are not limited to, bags, boxes or cartons, bottles, packages of any type or design or material, over-wrap, shrink-wrap, affixed components (e.g., stapled, adhered, or the like), or combinations of any of the foregoing. For example, a single package kit may provide containers of individual compositions and/or food compositions physically associated such that they are considered a unit for manufacture, distribution, sale, or use.

The term "virtual package" means that the components of a kit are associated by directions on one or more physical or virtual kit components instructing the user how to obtain the other components, e.g., in a bag or other container containing one component and directions instructing the user to go to a website, contact a recorded message or a fax-back service, view a visual message, or contact a caregiver or instructor to obtain, for example, instructions on how to use the kit, or safety or technical information about one or more components of a kit. Examples of information that can be provided as part of a virtual kit include instructions for use;

safety information such as material safety data sheets; poison control information; information on potential adverse reactions; clinical study results; dietary information such as food composition or caloric composition; general information on cognitive, behavioral, or motor function; diseases that affect cognitive, behavioral, or motor function; treating cognitive, behavioral, or motor function; or general information on treatment or preservation of cognitive, behavioral, or motor function; self-help relating to cognitive, behavioral, or motor function; caregiver information for those caring for animals with cognitive, behavioral, or motor function challenges; and use benefits, and potential side-effects or counter-indications for cognitive drugs.

All percentages expressed herein are by weight of the composition on a dry matter basis unless specifically stated otherwise. The skilled artisan will appreciate that the term "dry matter basis" means that an ingredient's concentration or percentage in a composition is measured or determined after any free moisture in the composition has been removed.

As used throughout, ranges are used herein in shorthand, so as to avoid having to set out at length and describe each and every value within the range. Any appropriate value within the range can be selected, where appropriate, as the upper value, lower value, or the terminus of the range.

Where used herein, the term "about" indicates that the given value, plus or minus 10%, is intended. "About" is thus used a shorthand to reflect the recognition that small variations from the literal value stated are still within the scope of the invention. Where "about" is used in conjunction with the dextrose equivalent (DE.), generally if the foregoing definition does not reasonably apply, the stated value plus or minus 1 full integer is intended, e.g., a "DE of about 5" includes compounds with DE from 4 to 6.

As used herein and in the appended claims, the singular form of a word includes the plural, and vice versa, unless the context clearly dictates otherwise. Thus, the references "a", "an", and "the" are generally inclusive of the plurals of the respective terms. For example, reference to "a puppy", "a method", or "a food" includes a plurality of such "puppies", "methods", or "foods". Reference herein, for example to "an antioxidant" includes a plurality of such antioxidants, whereas reference to "pieces" includes a single piece. Similarly, the words "comprise", "comprises", and "comprising" are to be interpreted inclusively rather than exclusively. Likewise the terms "include", "including" and "or" should all be construed to be inclusive, unless such a construction is clearly prohibited from the context. Where used herein "examples," or "for example," particularly when followed by a listing of terms, is merely exemplary and illustrative, and should not be deemed to be exclusive or comprehensive.

The methods and compositions and other advances disclosed here are not limited to particular methodology, protocols, and reagents described herein because they may be varied in ways that are apparent to the skilled artisan. Further, the terminology used herein is for the purpose of describing particular embodiments only, and is not intended to, and does not limit the scope of that which is disclosed or claimed.

Unless defined otherwise, all technical and scientific terms, terms of art, and acronyms used herein have the meanings commonly understood by one of ordinary skill in the art in the field(s) of the invention, or in the field(s) where the term is used. Although any compositions, methods, articles of manufacture, or other means or materials similar or equivalent to those described herein can be used in the practice of the present invention, certain preferred compositions, methods, articles of manufacture, or other moans or materials are described herein.

All patents, patent applications, publications, technical and/or scholarly articles, and other references cited or referred to herein are in their entirety incorporated herein by reference to the extent allowed by applicable law. The discussion of those references is intended merely to summarize the assertions made therein. No admission is made that any such patents, patent applications, publications or references, or any portion thereof, are relevant, material, or prior art. The right to challenge the accuracy and pertinence of any assertion of such patents, patent applications, publications, and other references as relevant, material, or prior art is specifically reserved. Full citations for publications not cited within the specification are set forth at the end of the specification.

The Invention

In a first aspect, the invention provides compositions suitable for influencing recovery from strenuous physical activity in animals. The compositions generally comprise one or more sources of carbohydrate, one or more sources of protein, and optionally one or more antioxidants. More particularly, the compositions comprise about 4% to 6% readily-absorbable carbohydrate, about 10% to 30% maltodextrins, and about 20% to 50% starch, for a total of about 40% to 80% carbohydrate. The compositions also comprise about 20% to about 40% protein from one or more sources; and optionally one or more antioxidants.

In one embodiment, the readily absorbable carbohydrate is a monosaccharide or disaccharide that can raise blood glucose levels quickly after ingestion by an animal. Examples of readily absorbable carbohydrates used herein include dextrose, fructose, galactose, xylose, ribose, sucrose, or combinations thereof.

The maltodextrins of the composition comprise one or more maltodextrins with a dextrose equivalent (DE) from about 5 to 20. As the skilled artisan will appreciate, a variety of maltodextrins are encompassed in the formula, and they tend to provide functionality according to the complexity as indicated by the particular DE. The lower the DE, the more complex the carbohydrate. In one embodiment, the maltodextrin of the compositions comprises a three or more maltodextrins each having different properties. In one preferred embodiment, the composition features a maltodextrin with a DE of about 5, a maltodextrin with a DE of about 10, and a maltodextrin with a DE of about 20. In a presently preferred embodiment, each of the maltodextrins are selected for slightly different effects on blood sugar in the animal, They may be present in any relative proportion. In one embodiment, the composition comprises about 30 to 40% of each of the maltodextrins.

The starch in the composition can be any starch or starch-containing material known in the art. Preferably, the starch is provided by one or more of rice flour, wheat flour, or a modified starch. Preferably, the starch will provide a prolonged source of carbohydrate to enhance blood glucose as compared to the much more absorbable carbohydrates such as dextrose and the maltodextrins.

In a presently preferred embodiment, the composition is as fellows with respect to the major carbohydrate portion: the readily absorbable carbohydrate comprises dextrose, the maltodextrins comprise at least one maltodextrin each of DE about 3, DE about 10, and DE about 20, and the starch is provided by one or more of rice flour, wheat flour, or modified starch.

The composition also comprises One or more sources of protein. The protein can be from any source whether animal, plant, microbial, or other. Preferably each such protein is digestible as determined for example by the PD score. Also preferably each individual source, or the protein sources collectively, are of high quality, and provide good biological value, as determined for example by the BV, PER, AAS, or PDCAAS scores. Examples of proteins suitable for use herein include proteins from meat or dairy sources, proteins from grains, soy or other plants, and microbial proteins.

In one embodiment the one or more sources of protein comprise whey protein, corn gluten, or combinations thereof. The whey protein comprises a whey protein concentrate or Whey protein isolate. Preferably, a whey protein concentrate with about 80% crude protein is included. The composition comprising corn gluten preferably comprises corn gluten meal, for example With about 75% crude protein.

In certain embodiments, the composition comprises about equal amounts of a plant protein and an animal protein to provide, for example, a preferred amino acid balance to the composition for influencing recovery. In one embodiment, the protein comprises about 10% to about 15% whey protein concentrate having about 80% crude protein, and about 10% to about 15% corn gluten meal having about 75% crude protein.

In some embodiments, to mitigate damage from oxidative stress, the composition contains antioxidants. In certain embodiments, the composition comprises from about 1% to about 15% antioxidants, preferably about 2% to about 15%, more preferably about 3% to about 12% total antioxidants. Preferably, the antioxidants comprise one or more carotenoids. Preferred antioxidants include the marine algae. *Haematococcus pluvialis*, an carotenoid-containing *Haematococcus pluvialis* extract, astaxanthin, lutein, or combinations thereof.

In one embodiment, the compositions comprise about 4% to 6% readily-absorbable carbohydrate; about 10% to 30% maltodextrins; and about 20% to 50% starch, for a total of about 40% to 80% carbohydrate; about 20% to about 40% protein; and from about 1% to about 15% total antioxidants.

The composition can be adapted for use in any form as food (including beverage or drink) or feed. The compositions are well suited for use as human or pet food or as a pet treat or reward, or a snack food for humans. The compositions are also well suited for use as dietary supplements, or can be formulated as meal replacements, or as nutritionally balanced foods. In a presently preferred embodiment, the composition is a pet food or pet treat, for example, a pet treat in the form of a biscuit. In another embodiment, the composition is in the form of kibble a for companion animal, such as a dog or cat. In another embodiment, the composition is in the form of powder, in which a mixture of two or more of the dry ingredients can be combined at home With the addition of water or other liquid ingredients and baked to form a biscuit, or an uncooked dough that includes some or all of the ingredients and baked to form a biscuit.

In various embodiments, the composition further comprises one or more additional amino acids or their salts or derivatives, for example, glutamine, glutamic acid, one or more BCAA (leucine, isoleucine, or valine), or arginine. Each of these amino acids is considered to play a role in influencing recovery from strenuous activity. The skilled artisan will appreciate the metabolic and energetic utilization of these amino acids during and after physical activity in an animal. For example, glutamine is an amino acid essential for many important homeostatic functions and for the optimal functioning of a number of tissues in the body, particularly the immune system and the gut however, during various Catabolic states, (e.g., strenuous physical activity such as exercise, infection, and trauma), glutamine homeostasis is placed under stress and glutamine reserves, particularly in the skeletal muscle, are depleted. For glutamine metabolism, strenuous physical activity stress is basically the same as other catabolic stresses. Plasma glutamine responses to both prolonged and high intensity physical activity are characterized by increased levels during the activity followed by significant decreases during the post-activity recovery period. Generally, several hours of recovery are required for restoration of pre-activity levels, depending on the intensity and duration of the activity. If recovery between activity sessions is inadequate, the acute effects of the activity on plasma glutamine level may be cumulative, overload training has been shown to result in low plasma glutamine levels requiring prolonged recovery. Athletes suffering from the overtraining syndrome (OTS) appear to maintain low plasma glutamine levels for months or years. Thus, the inventors have determined that providing additional amounts of one or more of the six foregoing amino acids, glutamine, glutamic acid, one or more BCAA (leucine, isoleucine, or valine), or arginine, may be advantageous for recovery, for example by shifting from protein catabolism to protein biosynthesis by both insulin-dependent and insulin-independent means, by having a sparing effect on loss of an amino acid or protein such as muscle protein, by providing one or more intermediates for energetic or biosynthetic purposes, such as TCA cycle intermediates, by stimulating glycogen recovery by both insulin-dependent and insulin-independent means.

The composition may further comprise one or More recovery agents. Recovery agents include antioxidants such as vitamin C, vitamin F, or vitamin A; compounds such as glutamine, succinate or its salts or derivatives, various enzyme co-factors (e.g., coenzyme Q10), MCTs, electrolytes such as sodium, potassium, herbal supplements or extracts, and the like. In some embodiments, the compositions described herein may also be administered or taken in conjunction with such recovery agents, rather than, or in addition to comprising them. Recovery agents can also aid with the hydration or rehydration of the animal, as well as the oxygenation or reoxygenation of the animal's blood.

In a second aspect, the invention provides compositions suitable for influencing recovery from strenuous physical activity in an animal. The compositions comprise (a) about 4% to 6% of a, first carbohydrate component having a dextrose equivalent (DE) of greater than about 85 to 100; (b) about 10% to 30% of a second carbohydrate component having a DE between about 5 and 20; (c) about 20% to 50% of a third carbohydrate component having a DE of less than about 5. The compositions comprise about 40% to 80% of said first, second, and third carbohydrates Combined. The compositions further comprise (d) one or more sources of amino acids, wherein glutamine, glutamic acid, lencine, isoleucine, valine, and arginine, collectively comprise about 40% to 55% of the total amino acids provided by said sources. It should be noted that the compositions comprise about 10% to 20% glutamine, glutamic acid, leucine, isoleucine, valine, and arginine combined. The compositions also comprise (e) an antioxidant component comprising one or more carotenoids.

As with the compositions of the first aspect, the antioxidant component preferably comprises astaxanthin, lutein, *H. pluvialis*, an extract from *H. pluvialis*, or any combination thereof.

In one embodiment, about 15% to 30% of the total amino acid content in the composition is the branched-chain amino acids (BCAA), i.e. leucine, isoleucine, and yahoo. In a presently preferred composition, about 10% to 20% of the total amino acid content is leucine.

In other embodiments, about 2% to 5% of the total amino acid content in the composition is arginine, and/or about 15% to 30% of the total amino acid content is glutamine and glutamic acid. Moreover, the composition in one embodiment of the foregoing is such that about 4% to 7.5% of the total amino acid content is glutamine.

The composition of the second aspect contains carbohydrates generally in accordance with the compositions of the first aspect provided above. Thus, preferably, the first carbohydrate component comprises one or more of dextrose, fructose, galactose, xylose, ribose, sucrose, or combinations thereof. In one presently preferred embodiment, the first carbohydrate component consists essentially of dextrose. The second carbohydrate component generally comprises one or more maltodextrins, each such maltodextrin having a different DE, while the third carbohydrate component comprises a starch, modified starch, or flour.

The composition comprises one or more sources of amino acids, such as at least one protein, protein hydrolyzate, peptide, or amino acid. The skilled artisan will appreciate that any combination of the foregoing, and many such sources of amino acids are available commercially. "Protein hydrolyzate" comprises varying degrees of hydrolysis of proteins or peptides, by any known or acceptable method for use in food compositions.

In one embodiment, one or more sources of amino acids comprise an animal protein and a plant protein, or a hydrolyzate thereof. Whey protein and corn gluten are sometimes used herein as sources of amino acids. The sources of amino acids, or the selected proteins can be used in approximately equal amounts, or can be used in amounts to optimize the desired amino acid content of the composition, e.g., by blending the amino acid sources based on the amino acid profile of each.

The composition in one embodiment comprises 10% to 15% whey protein concentrate flaying about 80% crude protein, and 10% to 15% corn gluten meal having about 75% crude protein. The composition preferably also comprises about 4% to 6% dextrose, about 10% to 30% maltodextrins, about 20% to 50% starch, and at least one of astaxanthin, lutein, *H. pluvialis*, or an extract thereof. The maltodextrins preferably comprise 30% to 40% each of a carbohydrate having a DE of about 5, a carbohydrate having a DE of about 6 to 10, and a carbohydrate having a DE of from about 10 to 20.

As above, the compositions can be readily formulated for use in humans and companion animals. They can be formulated as snack foods, energy bars, pet food, pet treats, dietary supplements, nutritionally balanced foods and the like. They can also be readily formulated for use in beverages, shakes, and the like, or as gels, foams or in other convenient or appealing forms, or in forms which can be readily administered before, during or after strenuous physical activity.

In a third aspect, the invention provides compositions for influencing recovery from strenuous activity. These compositions differ in scope and composition but share similar features with the first two aspects of the invention. The compositions comprise (a) 20% to 40% protein mixture, said protein mixture comprising whey protein and corn gluten; (b) about 4% to 6% of a first carbohydrate component having a dextrose equivalent (DE) of about 85 to 100; (c) about 10% to 30% of a second carbohydrate component having a DE of about 5 to 20, (d) 20% to 50% of a third carbohydrate component having a DE less than 5, and (e) an antioxidant component comprising at least one carotenoid.

The first, second, and third carbohydrate components have the features in common with those of the second aspect of the invention. Preferably, the first carbohydrate component comprises dextrose, the second carbohydrate component comprises one or more maltodextrins, each having different DE, and the third carbohydrate component comprises a starch, or modifier starch. The compositions comprise about 40% to 80% of the first, second and third carbohydrate components combined.

The composition comprises whey protein that is preferably provided by a whey protein concentrate or isolate, and the corn gluten is preferably provided by corn gluten meal. In one embodiment, the composition comprises about the equal amount of the whey protein concentrate (or isolate) as it does corn gluten meal. The whey protein concentrate and corn gluten mean are about 80% and 75% protein content, respectively, based on crude protein analysis, in a presently preferred embodiment.

Preferably, the composition features about 15% to 30% of the total amino acid content as the branched-chain amino acids, leucine, isoleucine, and valine, about 15% to 30% as glutamine and glutamic acid, and about 2% to 0.5% as arginine. The foregoing amino acids combined are preferably about 40% to 55% of the total amino acids. In various embodiments, about 10% to 20% of the total amino acid content is leucine, and/or about 4% to 7.5% of the total amino acid content is glutamine.

The composition of this aspect, as with the others can be formulated for any animal, in any form for administration as a food, snack, pet food, pet treat, or the like.

Also provided herein are methods for influencing recovery in animals, from a physical activity, particularly a strenuous physical activity. The methods are suited for use with any of the compositions described herein, for example in the first through third aspects of the invention.

Generally the methods provided are far influencing recovery from strenuous physical activity in an animal. The methods comprise administering to an animal within a time period of about 90 minutes before the start of the physical activity to about 90 minutes after the completion of the physical activity, an effective amount of a composition provided herein. In one embodiment, the preferred composition for administration comprises (a) about 4% to 6% of a first carbohydrate component having a dextrose equivalent (DE) of greater than about 85 to 100; (b) about 10% to 30% of a second carbohydrate component having a DE between about 5 and 20; (c) about 20% to 50% of a third carbohydrate component having a DE of less than about 5. The composition comprises about 40% to 80% of the first, second, and third carbohydrate components combined. It also comprises (d) one or more sources of amino acids. Preferably glutamine, glutamic acid, leucine, isoleucine, valine, and arginine, collectively comprise about 40% to 55% of the total amino acids provided by the one or more sources of amino acids. The composition preferably comprises about 10% to 20% glutamine, glutamic acid, leucine, isoleucine, valine, and arginine combined. The composition also comprises (e) am antioxidant component comprising one or more carotenoids.

In one embodiment, the first carbohydrate component consists essentially of dextrose, although other mono- or di-saccharides that are readily absorbed and help to quickly raise blood sugar in an animal, may be used. The second carbohydrate component comprises at least a first maltodextrin having a DE of about 5, a second maltodextrin having a DE of about 10, and a third maltodextrin having a DE of about 20, Preferably, the first, second, and third maltodextrins each comprise about equal proportions (e.g., about 30% to 40% each by weight) of the second carbohydrate component.

The method provides for administration of a composition wherein preferably, of the total amino acid content in the composition, about 15% to 30% is branched-chain amino acids, leucine, isoleucine, and valine, about 15% to 30% is glutamine and glutamic acid, and about 2% to 5% is arginine. About 10% to 20% of the total amino acid content in the composition is leucine in one embodiment. About 4% to 7.5% of the total amino acid content in the composition is glutamine in another.

The method provides for administration of an effective amount of the composition for influencing recovery. The effective amount required is an amount sufficient to reduce at least one symptom of damage from strenuous physical activity so as to hasten recovery in the animal from the strenuous physical activity, or improve the extent of recovery, relative to a control animal that is not administered the composition.

In various embodiments, the symptom of damage comprises any one or more of loss of integrity of a membrane, alteration in blood concentrations of one or more liver or muscle enzymes indicative of localized or systemic stress, oxidative stress or increase in oxyl- or peroxyl-radicals, alterations in blood calcium, potassium, or other ions, damage to one or more cells, muscle fiber damage, depletion of glycogen stores, low blood glucose, protein catabolism, or depletion of one or more amino acids, lactate build-up or low rate of lactate clearance, pH changes indicative of stress, oxygen debt, increase in one or more stress hormones indicative of localized or systemic stress, inflammation, fatigue, or soreness.

Further, relative to a control animal not receiving the composition, the composition preferably influences recovery, at least in part, by one or more of the following mechanisms or actions: raising blood glucose levels, lowering blood lactate or improving lactate clearance, replenishing glycogen stores, reducing oxidative stress or quenching radicals, reducing membrane damage, maintaining or improving membrane integrity, maintaining or improving blood concentration of at least one amino acid that is metabolized during strenuous physical activity, reducing activity-induced protein catabolism, increasing protein biosynthesis, helping maintain blood oxygenation, reducing the production of at least one stress hormone, reducing fatigue or reducing soreness.

The method can be used in any animal or group of animals that participate in or are subjected to strenuous activity such as exercise, training, competitive sports, and the like. The method is useful with human and companion animals. The method encompasses compositions formulated for consumption by either or both human or companion animals. Presently preferred animals are humans and dogs, particularly working dogs, competing dogs, or dogs that accompany their human caretakers on for example, walking, jogging, hiking, or running.

The methods, encompass administration of the novel composition for influencing recovery in conjunction with one or more recovery agents as described herein. The administration of the composition for influencing recovery can precede, be simultaneous or sequential with, or can follow the administration of the recovery agent(s). For example, a novel composition may be administered in accordance with the method after the completion of the strenuous activity or exercise. A separate recovery agent in the form of a food composition, medicament, dietary supplement, beverage or the like may be taken prior to the start of the physical activity in conjunction with the administration of the composition for influencing recovery provided herein. Similarly, either or both the composition and the recovery agent may be taken before the start of, during, or after the completion of the physical activity. The recovery agent, depending on its nature, may be taken well outside of the 2-hour window before and after exercise for the administration of the novel composition, the recovery agent may have a window of 8 to 12, 24, 48, or even 72 hours before or after the strenuous activity to be taken in conjunction with the compositions provided herein.

Other aspects of the invention feature kits for influencing recovery of an animal from strenuous physical activity, and kits for preparing a composition of the invention. The kits for influencing recovery comprise in separate containers in a single package or in separate containers in a virtual package (1) a composition comprising (a) about 4% to 6% of a first carbohydrate component having a dextrose equivalent (DE) of greater than about 85 to 100; (h) about 10% to 30% of a second carbohydrate component having a DE between about 5 and 20; (c) about 20% to 50% of a third carbohydrate component having a IDE of less than about 5; wherein the composition comprises about 40% to 80% of said first, second, and third carbohydrates combined; (d) one or more sources of amino acids, wherein glutamine, glutamic acid, leucine, isoleucine, valine, and arginine, collectively comprise about 40% to 55% of the total amino acids provided by said sources, wherein the composition comprises about 10% to 20% glutamine, glutamic acid, leucine, isoleucine, valine, and arginine combined; and (e) an antioxidant component comprising one or more carotenoids; and (2) instructions for using the composition for influencing recovery from strenuous physical activity in an animal that has or is about to undergo such physical activity.

The kits further or optionally comprise one or more recovery agents, additional compositions, or medicaments for influencing recovery from strenuous physical activity or for treating or mitigating damage resultant from strenuous physical activity in animal. The kits also Optionally or further comprise additional instructions for using the recovery agents, additional compositions, or medicaments in conjunction with the composition for influencing recovery from strenuous physical activity in an animal that has or is about to undergo such physical activity.

The components of the kits featuring one or more additional recovery agents or the like may be administered together, or in conjunction with each other in accordance with the methods as described herein. The kits can be directed to influencing recovery in humans or in animals such as companion animals. The kits may be designed for convenience, e.g., for example featuring take-along aspects such as a carrying case for transporting the composition to a remote location where an animal needing to recover from strenuous activity is located.

The kits for preparing a composition for influencing recovery of an animal from strenuous physical activity, comprise, in separate containers in a single package or in separate containers in a virtual package, for every 100 g of composition to be prepared (1) about 4 to 6 g of a first carbohydrate component having a dextrose equivalent (DE) of greater than about 85 to 100; (2) about 10 to 30 g of a second carbohydrate component having a DE between about 5 and 20; (3) about 20 to 50 g of a third carbohydrate component having a DE of less than about 5; such that the composition to be prepared comprises about 40 to 80 g of said first, second, and third carbohydrates combined; (4) one or more sources of amino acids, wherein glutamine, glutamic acid, leucine, isoleucine, valine, and arginine, collectively comprise about 40% to 55% of the total amino acids provided by said sources, such that the composition to be prepared comprises about 10 to 20 g glutamine, glutamic acid, leucine isoleucine, vane, aid arginine combined; and (5) 1 to 12 g of an antioxidant component comprising one or more carotenoids.

The kits further Or Optionally comprise instructions for one or more of using the kit for preparing the composition, administering the composition to an animal, or using the composition to influence recovery from strenuous activity. A vessel, howl or container, or the like can be provided in the kits for admixing the package contents to prepare the composition. For example a simple disposable, flexible mixing bag with a reclosable or zip-type fastener may be very useful for admixing the components. Alternatively, the kit may include instructions for admixing the components as they are consumed such that the composition is formed in the animal at the time of administration.

Still other aspects provided herein include means for communicating information about, or instruction for use of, a composition for influencing recovery from strenuous physical activity. The information is communicated particularly about compositions comprising (a) about 4% to 6% of a first carbohydrate component having a dextrose equivalent (DE) of greater than about 85 to 100; (b) about 10% to 30% of a second carbohydrate component having a DE between about 5 and 20; (c) about 20% to 50% of a third carbohydrate component having a DE of less than about 5; wherein the composition comprises about 40% to 80% of said first, second, and third carbohydrates combined: (d) one or more sources of amino acids, wherein glutamine, glutamic acid, leucine, isoleucine, valine, and arginine, collectively comprise about 40% to 55% of the total amino acids provided by said sources, wherein the composition comprises about 10% to 20% glutamine, glutamic acid, leucine, isoleucine, valine, and arginine combined; and (e) an antioxidant component comprising one or more carotenoids. The information communicated by the described means is about, or the instructions are for, one or more of (1) instructions for administering the composition to an animal that is about to undergo or has recently undergone strenuous physical activity; (2) instructions for one or more methods of using the composition for the benefit of an animal that is, has recently been, or will soon be, subject to strenuous physical activity; (3) information on providing proper nutrition, including the composition, to an animal that has recently been, or soon will be subject to strenuous physical activity; (4) information about physical activity or strenuous physical activity; (5) information regarding physical, cellular and biochemical results of strenuous physical activity, symptoms of damage resulting from strenuous physical activity, or recovery from such activity; or (6) comparative information or test results regarding the composition, wherein the means of communicating comprises a physical or electronic document, digital storage media, optical storage media, audio presentation, audiovisual display, or visual display containing the information or instructions.

In various embodiments, the communication means is selected from the group consisting of a displayed web site, visual display kiosk, brochure, product label, package insert, advertisement, handout, public announcement, audiotape, videotape, DVD, CD-ROM, computer readable chip, computer readable card, computer readable disk, USB device. FireWire device, computer memory, and combinations thereof.

Also provided herein is a package comprising a composition of the invention and a label, logo, graphic, symbol slogan, or the like identifying the package and composition within as useful for influencing recovery from strenuous physical activity in an animal. In one embodiment, the package comprises a composition having about 4% to 6% of a first carbohydrate component having a dextrose equivalent (DE) of greater than about 85 to 100; about 10% to 30% of a second carbohydrate component having a DE between about 5 and 20; about 20% to 50% of a third carbohydrate component having a DE of less than about 5; wherein the composition comprises about 40% to 80% of said first, second, and third carbohydrates combined; one or more sources of amino acids, wherein glutamine, glutamic acid, leucine, isoleucine, valine, and arginine, collectively comprise about 40% to 55% of the total amino acids provided by said sources, wherein the composition comprises about 10% to 20% glutamine, glutamic acid, leucine, isoleucine, valine, and arginine combined; and an antioxidant component comprising one or more carotenoids; the package containing a word or words, picture, design, logo, graphic, symbol, acronym, slogan, phrase, or other device, or combinations thereof, either directly on the package or on a label affixed thereto, indicating that the contents of the package is useful for influencing recovery from strenuous physical activity in an animal.

Preferably, such device comprises the words "improves recovery from exercise", "improves recovery", "reduces fatigue after strenuous activity", or an equivalent expression printed on the package. Any package or packaging material suitable for containing the composition is useful in the invention, e.g., a bag, box, bottle, can, pouch, and the like, manufactured from paper, plastic, foil, metal, and the like. In a preferred embodiment, the package contains a food composition adapted for a particular animal such as a human, canine or feline, as appropriate for the label, preferably a companion animal food composition.

In another aspect, the invention provides for use of one or more composition provided herein to prepare a medicament for influencing recovery from strenuous physical activity, reducing or preventing damage or symptoms of such activity, reducing or preventing recovery time, increasing energy, maintaining blood glucose during or after exercise or activity, facilitating replenishment of glycogen stores, reducing fatigue or inflammation resultant from physical activity, retarding muscle soreness, preventing or treating exercise-induced muscle fiber damage, and preventing lactate buildup in an animal. The medicament can further comprise one or more recovery agents, vitamins, electrolytes, antioxidants, herbal extracts, NSAIDs, analgesics or pain medication, or combinations thereof. Generally, medicaments are prepared by admixing a compound or composition With excipients, buffers, binders, plasticizers, colorants, diluents, compressing agents, lubricants, flavorants, moistening agents, and other ingredients known to skilled artisans to be useful for producing medicaments and formulating medicaments that are suitable for administration to an animal.

These and other aspects of the invention Will be further illustrated by the following working examples which are included to augment, not limit, the understanding and communication of the invention as expressed in the appended claims.

EXAMPLES

The invention can be further illustrated by the following examples, although it will be understood that the examples are included merely for purposes of illustration and are not intended to limit the scope of the invention unless otherwise specifically indicated.

Example 1

A series of studies were conducted to assess the efficacy of food product, for influencing recovery from strenuous physical activity, such as exercise recovery in animals. The food products were evaluated for the ability in improving physical recovery, improving muscle glycogen replenishment, reducing muscle damage, stimulating protein synthesis, reducing catabolism, and reducing oxidative stress following exercise in dogs.

Methodology

A first study (Trial 1) evaluated n=10 dogs in a crossover design to test the feeding of a "performance" biscuit compared to a control that did not receive a biscuit. The "performance" biscuit contained multiple sources of carbohydrates, multiple sources of protein, and algae (*Haematococcus pluvialis*) as a source of carotenoids, particularly astaxanthin. During week 1, ten dogs were exercised on each of 3 days for various lengths of time on each day. One group of five dogs were fed the performance biscuit alter exercise on all 3 days, whereas the other group of five dogs were not fed any biscuit. The following week, both groups (all ten dogs) were crossed-over to the opposite treatment group and exercised on each of 3 days, as in week 1.

The performance biscuit in Trial 1 was composed of carbohydrates comprising dextrose, maltodextrin with equal proportions of 5, 10, and 20 dextrose equivalents (DE), and raw rice flour as starch. It was also composed of protein comprising whey protein concentrate (80% protein by crude protein analysis) and corn gluten meal (75% protein by crude protein analysis). It was also composed of 0.5% *H. pluvialis* as a source of carotenoids. The performance biscuit was nutritionally-balanced with vitamins and minerals, and 3f fat as palm oil. When fed a performance biscuit following exercise, each dog received 60 g of biscuit.

Before, and immediately following exercise, various indicators of physical recovery, metabolic status, and glycogen replenishment were assessed. The indicators were assessed at the following time points before exercise on day 1 (Pre-Trial baseline), before exercise on day 3 (Pre-exercise), and Post Exercise as follows: immediately after exercise (0-min), 15-min, 30-min, 60-min, 90-min, 120-min, and 24-hr after exercise. At each time point, blood concentrations of glucose, lactate, lactate dehydrogenase (LDH), alanine transaminase (ALT), blood urea nitrogen (BUN), calcium ion ($Ca^{2+}$), potassium ion ($K^+$), and free amino acids were measured. The results are shown in Table L Referring to Table 1, the blood glucose levels of the dogs before the initiation of the Trial on day 1, and before initiation of exercise on day 3 were not different between biscuit or no-biscuit treated groups (Table 1A). Also, blood glucose levels did not differ between the treatment groups immediately (0-min) or 15-min post-exercise. However, after 15 minutes a difference could be seen. At 30, 60, 90, and 120 min post-exercise, blood glucose levels in dogs fed the performance biscuit were 11.2% to 16% higher, than those of the dogs not consuming a performance biscuit. By 24-hr after exercise, blood glucose levels were similar between groups. A complete repletion of muscle glycogen has previously been linked with an acute rise in blood glucose levels following exercise and consumption of a maltodextrin-containing meal, see WO 2004077961A1.

As can be seen from Table 1, blood lactate levels also did not differ on day 1 or before initiation of exercise on day 3 (Table 1A). Lactate levels in the dogs' blood did rise with exercise in both groups, but lactate levels in dogs consuming the performance biscuit were 11.3% and 17.3% lower immediately (0 min) and 15-min, respectively, following exercise. Also, at 30 minutes, blood lactate levels in the biscuit-consuming group were significantly lower (34.4%) than those of the group receiving no biscuit. By 30 minutes, the blood lactate in the treatment group had returned to levels similar to baseline levels, i.e., before the initiation of exercise. Blood lactate levels did not diminish to baseline levels in the control group that did not receive the biscuit product until 60-min after exercise. Increased lactate levels contribute to fatigue; therefore, decreasing blood lactate levels can improve both endurance and recovery. The biscuit provided not only a 30-min advantage to recovering from the elevated levels of blood lactate, but diminished lactate levels over 30% in addition, the maximum blood lactate levels reached in the biscuit-receiving group were about 12% less than the maximum lactate level in the untreated dogs. Minimizing the maximum blood lactate levels may also have a positive outcome on minimizing damage and improving recovery from strenuous exercise.

Lactate dehydrogenase (LDH) is a muscle enzyme responsible for ultimately converting glucose into lactate. LDH enzyme activity in the blood is a marker of exercise-induced muscle cell leakage, and resultant decompartmentalization. As with the blood lactate levels, LDH levels at 15- and 30-min following exercise were lower in the biscuit-treated dogs by 17% and 8%, respectively (Table 1A). Also as with lactate, the maximum level of LDH observed in the control group was higher (113%) than that seen in the performance biscuit treatment group. Minimizing muscle cell leakage in the animal would also be expected to minimize damage that may occur and to have a positive influence on recovery from any such damage.

TABLE 1A

|  | Biscuit | No-biscuit | SE |
|---|---|---|---|
| Glucose (mg/dL) | | | |
| Pre-Trial baseline | 103.6 | 106.0 | 5.2 |
| Pre-exercise | 105.7 | 106.2 | 5.2 |
| Post-exercise: 0-min | 123.8 | 124.8 | 5.2 |
| Post-exercise: 15-min | 90.6 | 91.6 | 5.2 |
| Post-exercise: 30-min | 98.0 | 88.1 | 5.2 |
| Post-exercise: 60-min | 100.2 | 89.9 | 5.2 |
| Post-exercise: 90-min | 103.7 | 91.4 | 5.2 |
| Post-exercise: 120-min | 107.8 | 92.9 | 5.2 |
| Post-exercise: 24-hr | 100.8 | 101.1 | 5.2 |
| Lactate (mg/dL) | | | |
| Pre-Trial baseline | 11.0 | 11.8 | 7.4 |
| Pre-exercise | 10.3 | 10.8 | 7.4 |
| Post-exercise: 0-min | 19.8 | 22.3 | 7.4 |
| Post-exercise: 15-min | 15.1 | 18.3 | 7.4 |
| Post-exercise: 30-min | 9.6 | 14.6 | 7.4 |
| Post-exercise: 60-min | 11.2 | 9.3 | 7.4 |
| Post-exercise: 90-min | 10.2 | 10.8 | 7.4 |
| Post-exercise: 120-min | 8.9 | 12.5 | 7.4 |
| Post-exercise: 24-hr | 11.0 | 11.3 | 7.4 |
| LDH | | | |
| Pre-Trial baseline | 71.7 | 51.6 | 8.4 |
| Pre-exercise | 45.3 | 39.1 | 8.4 |
| Post-exercise: 0-min | 82.4 | 77.4 | 8.4 |
| Post-exercise: 15-min | 77.4 | 93.3 | 8.4 |

TABLE 1A-continued

|  | Biscuit | No-biscuit | SE |
|---|---|---|---|
| Post-exercise: 30-min | 66.8 | 72.6 | 8.4 |
| Post-exercise: 60-min | 58.6 | 60.4 | 8.4 |
| Post-exercise: 90-min | 61.7 | 57.1 | 8.4 |
| Post-exercise: 120-min | 50.8 | 50.4 | 8.4 |
| Post-exercise: 24-hr | 38.8 | 41.7 | 8.4 |

Alanine transaminase (ALT) levels are largely reflective of liver status. Elevated levels of ALT are interpreted as liver cell leakage caused by metabolic or oxidative stress. With reference to Table 1B, before exercise was initiated on day 1, ALT levels were not different. Through the duration of the trial on day 3 up through 24 hours post-exercise, ALT levels were 5% to 10.4% lower in dogs fed the performance biscuit. Thus, lowered levels are an indicator of an improvement in the status of the liver in response to feeding a performance biscuit following exercise,

TABLE 1B

| ALT | Biscuit | No-biscuit | SE |
|---|---|---|---|
| Pre-Trial baseline | 61.3 | 63.0 | 11.8 |
| Pre-exercise | 80.2 | 84.5 | 11.8 |
| Post-exercise: 0-min | 83.9 | 91.1 | 11.8 |
| Post-exercise: 15-min | 83.9 | 89.3 | 11.8 |
| Post-exercise: 30-min | 80.8 | 86.5 | 11.8 |
| Post-exercise: 60-min | 79.6 | 88.1 | 11.8 |
| Post-exercise: 90-min | 81.2 | 89.0 | 11.8 |
| Post-exercise: 120-min | 79.9 | 89.2 | 11.8 |
| Post-exercise: 24-hr | 76.2 | 83.3 | 11.8 |

Blood urea nitrogen (BUN) is a measure of the metabolic end-products of nitrogen metabolism, particularly from protein or amino acid breakdown. BUN levels increased at all time points before and after exercise on day 3 in dogs consuming the biscuit (Table 1C). This indicates that the extra protein in the performance biscuit increased the amino acid content being absorbed and available to tissues for recovery and metabolism. A rise in BUN following the initiation of the Trial in the absence of the addition dietary protein (or amino acid) intake would indicate catabolism of tissue protein/amino acid stores. This would be expected to negatively influence recovery because the body would be in a catabolic state, which is not preferred for post-activity recovery. The BUN levels in the performance biscuit-treated dogs were 6% to 18% greater than BUN levels in the control dogs not receiving the biscuit. This indicates that the increased BUN level is from the biscuit protein metabolism.

TABLE 1C

| BUN | Biscuit | No-biscuit | SE |
|---|---|---|---|
| Pre-Trial baseline | 21.3 | 20.1 | 1.4 |
| Pre-exercise | 24.2 | 22.7 | 1.4 |
| Post-exercise: 0-min | 24.5 | 21.9 | 1.4 |
| Post-exercise: 15-min | 24.3 | 21.4 | 1.4 |
| Post-exercise: 30-min | 23.9 | 21.3 | 1.4 |
| Post-exercise: 60-min | 23.9 | 20.8 | 1.4 |
| Post-exercise: 90-min | 24.0 | 20.4 | 1.4 |
| Post-exercise: 120-min | 23.7 | 20.2 | 1.4 |
| Post-exercise: 24-hr | 23.0 | 22.4 | 1.4 |

Elevated blood levels of calcium and potassium indicate exercise-induced muscle cell leakage. As can be seen from Table 1D, on day 3, calcium levels were 2.4% to 4.7% lower in biscuit-fed dogs versus control dogs. Similarly, potassium levels were 2.2% to 4.5% lower from 15-min to 120-min after exercise in the biscuit-fed dogs.

TABLE 1D

|  | Biscuit | No-biscuit | SE |
|---|---|---|---|
| Ca |  |  |  |
| Pre-Trial baseline | 10.5 | 10.6 | 0.2 |
| Pre-exercise | 10.4 | 10.8 | 0.1 |
| Post-exercise: 0-min | 9.9 | 10.4 | 0.1 |
| Post-exercise: 15-min | 10.2 | 10.4 | 0.1 |
| Post-exercise: 30-min | 10.0 | 10.4 | 0.1 |
| Post-exercise: 60-min | 10.2 | 10.6 | 0.1 |
| Post-exercise: 90-min | 10.3 | 10.6 | 0.2 |
| Post-exercise: 120-min | 10.3 | 10.7 | 0.1 |
| Post-exercise: 24-hr | 10.8 | 11.1 | 0.1 |
| K |  |  |  |
| Pre-Trial baseline | 3.84 | 3.81 | 0.07 |
| Pre-exercise | 4.12 | 3.99 | 0.08 |
| Post-exercise: 0-min | 4.12 | 4.14 | 0.09 |
| Post-exercise: 15-min | 4.02 | 4.12 | 0.08 |
| Post-exercise: 30-min | 3.93 | 4.07 | 0.09 |
| Post-exercise: 60-min | 3.85 | 4.03 | 0.07 |
| Post-exercise: 90-min | 3.96 | 4.05 | 0.08 |
| Post-exercise: 120-min | 3.9 | 4.05 | 0.07 |
| Post-exercise: 24-hr | 4.02 | 3.93 | 0.08 |

Example 2

Methodology

The second study (Trial 2) evaluated a variation in the carbohydrate portion of the formula used in Trial 1. As in Trial 1, in Trial 2, 10 dogs in two groups were also used to test the feeding of a "performance" biscuit following a single bout of exercise. The biscuit-fed group (n=5) was compared to a no-biscuit control group (n=5). To test the efficacy of the modified biscuit formula, blood glucose levels were monitored to determine the dogs' glycemic response to consuming the biscuit immediately following exercise. All dogs were exercised on the same day and 5 of the 10 dogs were fed 60 g of biscuit immediately following exercise.

The "performance," biscuit contained multiple sources of carbohydrates and multiple sources of protein. The performance biscuit in Trial 2 was composed of carbohydrates comprising 5% dextrose, and 42.9% wheat flour (as starch). The biscuit also contained 13.3% maltodextrins. 61% of which was maltodextrin with a dextrose equivalent (DE) =20, and 39% was maltodextrin with DE=10, The biscuit was also composed of 29.5% protein comprising whey protein concentrate and corn gluten meal. It was also nutritionally balanced with vitamins and minerals, and 3% tallow as fat.

Immediately following exercise, glycemic response was monitored by assaying the dogs' glucose levels. Blood glucose was assessed 15-min, 30 min, and 60-loin after exercise. The results are shown in Table 2, Referring to Table 2, blood glucose levels in the dogs consuming the biscuit did not differ at any time (15, 30, or 60 min) after exercise and biscuit consumption compared to dogs not consuming the biscuit following exercise. The lack of glucose rise in the biscuit-treated dogs is largely a result of the reduced maltodextrin content and the increased starch content. No other variables were tested.

TABLE 2

| Glucose | Biscuit | No-biscuit | SE |
|---|---|---|---|
| Post-exercise: 0-min | 83.4 | 90.4 | 4.3 |
| Post-exercise: 15-min | 79.4 | 83.6 | 2.0 |
| Post-exercise: 30-min | 83.0 | 87 | 3.5 |
| Post-exercise: 60-min | 89.0 | 86 | 3.2 |

Example 3

Methodology

The third study (Trial 3) also evaluated a variation in the carbohydrate portion of the formula used in Trial 1. Trial 3 also used 10 dogs in two group to test the feeding of a "performance" biscuit following a single bout of exercise. The biscuit-fed group (n=5) was compared to a no-biscuit control group (n=5). To test the efficacy of the modified formula, blood glucose levels were monitored to determine the dogs' glycemic response to consuming the biscuit immediately following exercise. All dogs were exercised on the same day. The dogs in the biscuit-fed group were fed 60 g of biscuit immediately following exercise.

The "performance" biscuit contained multiple sources of carbohydrates and multiple sources of protein. The performance biscuit in Trial 3 was composed of carbohydrates comprising 5% dextrose, and 28.7% pre-cooked rice flour as starch. The biscuit also contained 32.6% maltodextrins, of which 40% had DE 20, 30% was DE-10, and 30% was DE=5. The biscuit was also composed of 29.5% protein comprising whey protein concentrate and corn gluten meal, having 80% and 75% protein, respectively. The biscuit formula was nutritionally balanced with vitamins and minerals, and had 3% tallow added a fat source.

Glycemic response was monitored by assaying the dogs' blood glucose levels. Blood glucose was assessed immediately after exercise (0-min), 15-min and 30-min after exercise. The results are shown in Table 3.

Referring to Table 3, blood glucose levels in the dogs consuming the biscuit increased at 15- and 30-min after biscuit consumption, as compared to dogs in the control that did not receive the biscuit following exercise. No changes were observed in the control group. No other variables were tested.

TABLE 3

| Glucose | Biscuit | No-Biscuit | SE |
|---|---|---|---|
| Post-exercise: 0-min | 113.4 | 106.4 | 2.2 |
| Post-exercise: 15-min | 122.6 | 105.0 | 4.0 |
| Post-exercise: 30-min | 122.4 | 106.8 | 5.0 |

Example 4

Methodology

The fourth study (Trial 4) evaluated a variation in the carbohydrate portion of the formula used in Trial 1. Trial 4 used 20 dogs in two groups to test the feeding of a "performance" biscuit following a single bout of exercise. The biscuit-fed group (n=10) was compared to a control group (n=10) that received no biscuit. To test the efficacy of the modified formula, blood glucose levels were monitored to determine the dogs' glycemic response to consuming the biscuit immediately following exercise. Five dogs from each group were exercised on the same day. The dogs from the biscuit-fed group were fed 60 g of biscuit immediately following exercise. The remaining dogs were exercised, and immediately thereafter the dogs from the biscuit-fed group were fed 60 g of biscuit.

The "performance" biscuit contained multiple sources of carbohydrates and multiple sources of protein. The performance biscuit in Trial 4 was composed of carbohydrates comprising 5% dextrose, and 29.4% raw rice flour as a starch. The biscuit composition also comprised 33.5% maltodextrin 40% of which was DE-20, 30% had DE=10, and 30% was DE-5. The biscuit was also composed of 30.5% protein comprising whey protein concentrate and corn gluten meal. It was nutritionally balanced with vitamins and minerals, and tallow was added to provide 3% fat.

Samples were taken for assaying the dogs' blood glucose levels as a means of monitoring glycemic response. Blood glucose was assessed from samples taken immediately following exercise (0-min), and at 15-min, 30-min, and 60-min after exercise. The results are shown in Table 4.

Referring to Table 4, blood glucose levels in the dogs consuming the biscuit increased over time, and at 15, 30, and 60 min after biscuit consumption were higher compared to dogs not receiving a biscuit following exercise.

TABLE 4

| Glucose | Biscuit | No-biscuit | SE |
|---|---|---|---|
| Post-exercise: 0-min | 96 | 97.7 | 3.5 |
| Post-exercise: 15-min | 104.3 | 96.6 | 4.7 |
| Post-exercise: 30-min | 109.6 | 97.2 | 4.1 |
| Post-exercise: 60-min | 100.8 | 93.8 | 4.3 |

Example 5

Methodology

The fifth study (Trial 5) evaluated a formula with a high level of fat, and moderate levels of protein and carbohydrates. Trial 5 used 20 dogs to test the feeding of a "performance" nibble administered following a single bout of exercise. The kibble-fed group (n=10) was compared to a control group (n=10) in which dogs received no feeding. To test the efficacy of the modified formula, blood glucose levels were monitored to determine the dogs' glycemic response to consuming the kibble immediately following exercise. Ten dogs were exercised on the same day, and 5 of the 10 dogs were fed 60 g of kibble immediately following exercise. A set of 10 different dogs were later exercised, and half were fed 60 g of kibble immediately. Glycemic response was monitored by assaying the dogs' blood glucose levels, Samples were taken immediately following exercise (0-min), and at 15-min, 30-min, and 60-min after exercise to assess blood glucose. The results are shown in Table 5, The "performance" kibble contained multiple sources of carbohydrates, fat, and protein. The performance kibble in Trial 5 was the commercial product, ProPlan Performance® with Chicken and Rice, composed of carbohydrates comprising 47% rice flour as starch. The kibble contained no maltodextrins or dextrose. The kibble was also composed of 30% protein comprising protein from chicken and corn gluten meal, and 20% fat. It was also nutritionally-balanced with vitamins and minerals.

Referring to Table 5, blood glucose levels in the dogs consuming the biscuit did not differ at any time (15, 30, or 60 min) after kibble consumption as compared to dogs not consuming anything following exercise. The lack of blood glucose rise in the kibble treated dogs is largely a result of the high fat and reduced maltodextrin content. No other variables were tested.

TABLE 5

| Glucose | Kibble | No-kibble | SE |
| --- | --- | --- | --- |
| Post-exercise: 0-min | 94.9 | 92.5 | 3.2 |
| Post-exercise: 15-min | 95.1 | 96.5 | 2.8 |
| Post-exercise: 30-min | 97.4 | 95.7 | 2.7 |
| Post-exercise: 60-min | 88.7 | 90.1 | 2.4 |

Example 6

Methodology

The sixth study (Trial 6) evaluated n=8 dogs in three different treatment groups to test feeding of a "performance" biscuit with or without *H. pluvialis* compared to a no-biscuit control. The "performance" biscuit contains multiple sources of carbohydrates, multiple sources of protein, and with or without algae (*H. pluvialis*) as a source of carotenoids, particularly astaxanthin ("astaxanthin"). Twenty four dogs were exercised for 3 days for various lengths of time on each day with a moderate level of exercise intensity. Eight dogs were fed the performance biscuit containing *H. pluvialis* after exercise on all 3 days, eight dogs were fed the performance biscuit without *H. pluvialis* after exercise on all 3 days, and eight dogs were not fed any biscuit: after exercise on all 3 days.

The performance biscuit was composed of carbohydrates comprising 5% dextrose, 32.3% maltodextrin with differing proportions of 5, 10, and 20 dextrose equivalents, and 28.5% pre-cooked rice flour as starch. The maltodextrins comprised 12.7% as 20 DE, 9.8% as 10 DE, and 9.8% as 5 DE. It was also composed of protein comprising 14.6% whey protein concentrate and 14.6% corn gluten meal. It was also composed of 0.48% *H. pluvialis* as a source of carotenoids, nutritionally balanced with vitamin and minerals as 0.72%, and 2.9% fat as tallow. The biscuit also contained 0.14% emulsifier, 0.25% salt, and 0.5% dry digest. Each dog received 60 g of biscuit.

Before and immediately following exercise, various indicators of physical recovery, metabolic status, and glycogen replenishment were assessed. The indicators were assessed before exercise and immediately after exercise on day 1, before exercise on day 3, immediately after exercise (0-min), 15-min, 30-min, 60-min, and 24-hr after exercise.

The glucose levels of the dogs were tested before the initiation of the trial on day 1, before initiation of exercise on day 3, and at several times immediately after exercise and biscuit ingestion. The results are shown in Table 6. The data shows that dogs fed the biscuit containing astaxanthin were able to better maintain a stable blood glucose level during and immediately following exercise compared to dogs not given a biscuit and dogs fed a biscuit without astaxanthin. It is believed that astaxanthin is effective at improving the efficient utilization of fat for energy metabolism during exercise, thus promoting aerobic metabolism and reducing the metabolic need for blood glucose from liver glycogen stores.

TABLE 6

| Glucose (mg/dL) | Biscuit With Astaxanthin | Biscuit Without Astaxanthin | No-biscuit Control | SE |
| --- | --- | --- | --- | --- |
| Pre-trial baseline | 100.3 | 105.1 | 104.7 | 2.2 |
| Pre-exercise | 89.3 | 99.4 | 98.1 | 2.4 |
| Post-exercise: 0-min | 79.9 | 61.4 | 59.2 | 6.6 |
| Post-exercise: 15-min | 83.2 | 81.5 | 52.7 | 4.1 |
| Post-exercise: 30-min | 88.4 | 81.2 | 53.5 | 4.1 |
| Post-exercise: 60-min | 79.3 | 79.8 | 53.5 | 3.7 |
| Post-exercise; 24-hr | 100.2 | 99.4 | 99.9 | 2.3 |

Lactate levels were also measured. The data is shown in Table 7. The levels did not differ on day 1 or before initiation of exercise on day 3. Lactate levels did rise with exercise in all groups and started to decline following exercise. However, dogs consuming the astaxanthin biscuits achieved pre-exercise lactate levels by 30-min post exercise. In comparison, dogs consuming the no-astaxanthin biscuit or control dogs did not achieve pre-exercise levels until 60 in post exercise. In addition, control dogs and no-astaxanthin dogs actually demonstrated an increase in blood lactate from 15-min to 30-min post exercise, whereas the astaxanthin-biscuit dogs had a continued decline to below pre-exercise levels. At 30-min after exercise, control dogs were on average 37.8% above, whereas no-astaxanthin biscuit dogs were only 12.7% above pre-exercise levels.)

This data further supports earlier observations that astaxanthin improves blood lactate levels after exercise and that improvements in blood lactate levels is a function of the ingesting astaxanthin. The improvement in blood lactate levels also provides evidence that the astaxanthin biscuit is promoting aerobic metabolism, such that excess glucose is not being metabolized into lactate, but that the Kreb's Cycle within the mitochondria is functioning, more efficiently to generate energy. This is likely occurring through the increased metabolism of fatty acids to support aerobic metabolism within the mitochondria.

TABLE 7

| Lactate (mg/L) | Biscuit With Astaxanthin | Biscuit Without Astaxanthin | No-biscuit Control | SE |
| --- | --- | --- | --- | --- |
| Pre-trial baseline | 1.00 | 1.00 | 0.96 | 0.11 |
| Pre-exercise | 1.16 | 1.09 | 0.99 | 0.09 |
| Post-exercise: 0-min | 1.71 | 1.67 | 1.75 | 0.18 |
| Post-exercise: 15-min | 1.24 | 1.17 | 1.29 | 0.12 |
| Post-exercise: 30-min | 1.12 | 1.22 | 1.36 | 0.16 |
| Post-exercise: 60-min | 0.90 | 0.87 | 0.77 | 0.12 |
| Post-exercise: 24-hr | 0.94 | 0.85 | 0.87 | 0.07 |

Calcium levels were also measured. The data is shown in Table 8. The elevated levels indicate exercise-induced muscle cell leakage. The data show that exercise-induced oxidative stress was reduced by the astaxanthin, which reduced damage to cells, most likely muscle cells, to reduce calcium leakage. Thus, astaxanthin is effective for optimizing exercise recovery.

Similarly, Gamma-glutamyl transferase (GGT) levels show that astaxanthin ingestion contributed to reducing oxidative stress induced by exercise in liver cells. On day 3, dogs fed the astaxanthin-containing biscuit were not different immediately following exercise and 15 min after exercise compared to pm-exercise levels. This is in contrast to control and no-astaxanthin biscuit dogs that demonstrated a 125% and 94% increase in GGT levels immediately after exercise. These elevated levels remained elevated through 24 hr after exercise. Also, immediately and 15 min after exercise, GGT levels were significantly lower in dogs fed astaxanthin biscuits compared to the control dogs.

TABLE 8

|  | Biscuit With Astaxanthin | Biscuit Without Astaxanthin | No-biscuit Control | SE |
|---|---|---|---|---|
| Ca |  |  |  |  |
| Pre-trial baseline | 10.20 | 10.46 | 10.46 | 0.11 |
| Pre-exercise | 10.26 | 10.40 | 10.39 | 0.13 |
| Post-exercise: 0-min | 10.00 | 9.81 | 10.08 | 0.18 |
| Post-exercise: 15-min | 9.74 | 10.15 | 10.19 | 0.17 |
| Post-exercise: 30-min | 10.13 | 10.13 | 10.38 | 0.21 |
| Post-exercise: 60-min | 10.31 | 10.55 | 10.54 | 0.14 |
| Post-exercise: 24-hr | 10.76 | 11.10 | 11.09 | 0.10 |
| GGT |  |  |  |  |
| Pre-trial baseline | 5.28 | 4.65 | 5.54 | 0.83 |
| Pre-exercise | 3.08 | 2.69 | 4.50 | 1.17 |
| Post-exercise: 0-min | 4.42 | 5.23 | 10.15 | 2.19 |
| Post-exercise: 15-min | 3.16 | 5.08 | 8.20 | 1.60 |
| Post-exercise: 30-min | 5.83 | 6.81 | 9.07 | 1.54 |
| Post-exercise: 60-min | 5.94 | 6.33 | 9.61 | 1.57 |
| Post-exercise: 24-hr | 6.56 | 6.99 | 9.36 | 1.39 |

In the specification, there have been disclosed typical preferred embodiments of the invention. Although specific terms are employed, they are used in a generic and descriptive sense only, and not for purposes of limitation. The scope of the invention is set forth in the appended claims. The skilled artisan will appreciate that many modifications and variations of the claimed invention are possible in light of the above teachings. It is therefore to be understood that within the scope of the appended claims the invention may be practiced otherwise than as specifically described.

What is claimed is:

1. A composition suitable for influencing recovery from strenuous physical activity in an animal comprising:
   about 4% to 6% readily-absorbable carbohydrate, the readily absorbable carbohydrate comprising dextrose;
   about 10% to 30% maltodextrins, the maltodextrins comprising a maltodextrin with a DE of about 5, a maltodextrin with a DE of about 10, and a maltodextrin with a DE of about 20;
   about 20% to 50% pre-cooked starch, the starch comprising rice flour, wheat flour, modified starch, or a combination thereof; and
   about 20% to about 40% protein;
   wherein the readily-absorbable carbohydrate, matlodextrins, and starch account for a total of about 40% to 80% carbohydrate of the composition.

2. The composition of claim 1, wherein the protein comprises whey protein, corn gluten, or combinations thereof.

3. The composition of claim 2, wherein the protein comprises about 10% to about 15% whey protein concentrate having about 80% crude protein, and about 10% to about 15% corn gluten meal having about 75% crude protein.

4. The composition of claim 1, further comprising one or more antioxidants.

5. The composition of claim 4, wherein the antioxidants comprise one or more carotenoids.

6. The composition of claim 1, suitable for use as a pet treat.

* * * * *